United States Patent
Wood et al.

(10) Patent No.: US 7,651,224 B2
(45) Date of Patent: Jan. 26, 2010

(54) DYNAMIC VISUAL VESTIBULAR ACUITY TESTING PROTOCOL

(75) Inventors: Scott Wood, Pittsburgh, PA (US); Alexander D Kiderman, Pittsburgh, PA (US)

(73) Assignee: Neuro Kinetics, Inc., Pittsburgh, PA (US)

( * ) Notice: Subject to any disclaimer, the term of this patent is extended or adjusted under 35 U.S.C. 154(b) by 0 days.

(21) Appl. No.: 11/930,573

(22) Filed: Oct. 31, 2007

(65) Prior Publication Data
US 2008/0151192 A1 Jun. 26, 2008

Related U.S. Application Data

(62) Division of application No. 11/181,019, filed on Jul. 13, 2005.

(60) Provisional application No. 60/587,345, filed on Jul. 13, 2004.

(51) Int. Cl.
*A61B 3/00* (2006.01)
*A61B 3/02* (2006.01)

(52) U.S. Cl. ........................... 351/246; 351/224

(58) Field of Classification Search ............... 351/222, 351/224, 246; 600/546; 606/5
See application file for complete search history.

(56) References Cited

U.S. PATENT DOCUMENTS

| | | | |
|---|---|---|---|
| 3,612,642 A | 10/1971 | Dostal | |
| 4,084,182 A | 4/1978 | Maiman | |
| 4,320,768 A * | 3/1982 | Ledley et al. | ............... 600/546 |
| 4,474,186 A * | 10/1984 | Ledley et al. | ............... 600/546 |
| 5,098,426 A * | 3/1992 | Sklar et al. | ..................... 606/5 |
| 5,130,838 A | 7/1992 | Tanaka et al. | |
| 5,304,112 A | 4/1994 | Mrklas et al. | |
| 5,652,756 A | 7/1997 | Stultz et al. | |
| 5,687,020 A | 11/1997 | Park et al. | |
| 5,821,521 A | 10/1998 | Bridgelall et al. | |
| 6,089,716 A * | 7/2000 | Lashkari et al. | ............. 351/221 |
| 6,247,813 B1 | 6/2001 | Kim et al. | |
| 6,275,718 B1 * | 8/2001 | Lempert | ..................... 600/407 |
| 6,299,308 B1 | 10/2001 | Veronka et al. | |
| 6,456,261 B1 | 9/2002 | Zhang | |
| 6,631,989 B2 | 10/2003 | Odom et al. | |
| 6,943,754 B2 | 9/2005 | Aughey et al. | |

* cited by examiner

*Primary Examiner*—Ricky L Mack
*Assistant Examiner*—James R Greece
(74) *Attorney, Agent, or Firm*—Blynn L. Shideler; Krisanne Shideler; BLK Law Group

(57) ABSTRACT

A compact neuro-otologic testing device and method provides an image producing laser with a right hand, servo controlled galvanometric based XY interface. The high quality closed loop servo control system that can drive the target (i.e. the laser image) in excess of 1,000,000 degrees/second$^2$ and at velocities in excess of 12000 degrees/second. The bandwidth of the XY interface is greater than 400 Hz, providing high image reproducibility. The repeatability and position accuracy of the target is +−3 arc-seconds and the field of range of the XY interface are about 60 degrees (i.e. about 60 degrees horizontal and 60 degrees vertical).

2 Claims, 4 Drawing Sheets

DYNAMIC VISUAL VESTIBULAR ACUITY TESTING PROTOCOL

RELATED APPLICATION

We, Scott Wood and Alexander Kiderman, have developed improvements in a dynamic visual-vestibular acuity testing protocol. This application is a divisional of U.S. patent application Ser. No. 11/181,019 filed Jul. 13, 2005 entitled "Compact Neuro-otologic, Neuro-opthalmologic Testing Device and Dynamic Visual Acuity Testing and Desensitization Platform" which published Oct. 19, 2006 as U.S. Patent Publication number 2006-0235331 and which claims the benefit of U.S. provisional patent application Ser. No. 60/587,345 entitled "Compact Neuro-otologic Testing Device" filed Jul. 13, 2005. The above identified publication is incorporated herein by reference.

BACKGROUND OF THE INVENTION

1. Field of the Invention

The present invention relates to a dynamic visual-vestibular acuity testing protocol that can utilize a compact rapid response laser light source capable of forming fast cycling (e.g. faster than 75 mille-seconds) shapes and images in which the motion of the display may be easily and precisely matched to the motion of the patient and the patient's eyes.

2. Brief Description of the Prior Art

Humans use three basic systems, namely visual, vestibular, and proprioceptive, to obtain a sense of balance in daily life. The three systems interact to maintain posture and impart a conscious sense of orientation in space. There are measurable reflexes associated with these stimulus modalities. Reflexes generally serve to maintain stability in posture (e.g. by extending muscle groups in the direction of an anticipated fall), or in maintaining stability of the visual field, thereby suppressing dizziness. A defect in one of these systems, or incongruous inputs amongst the systems can be compensated by a patient through reliance on the other two systems. However, such a defect decreases the patient's overall ability to adjust to incongruous stimuli between the other two fields. Also, a defect can result in a serious subjective feeling of disequilibrium in the affected patient until compensation for the deficit occurs.

Regarding the visual system, visual inputs aid in the maintenance of an upright posture and aid in orientation. Conscious and unconscious correction of posture is possible through processing of visual inputs. The adjustment of posture and sensation of movement in response to visual stimuli can be seen by observing individuals' responses to optokinetic stimuli (repeated movement of large objects in the subject's visual field). Such stimuli (e.g. a train moving on the adjacent platform) impart a sense of acceleration to the individual and lead to reflexive postural adjustments (e.g. leaning in the direction of the moving train) to maintain balance. Visual reflex arcs also aid in maintaining the stability of the visual field. The saccade system focuses a visual target of interest onto the fovea through a fast movement of the eyes. The smooth pursuit system allows fixation of gaze onto a moving object with a frequency of less than 1.2 Hz. The optokinetic reflex is a result of multiple objects moving through a patient's visual field (with the moving objects occupying about 80% of the patient's visual field). The optokinetic reflex imparts a sense of motion to the patient. It presents as a jerk nystagmus with the slow component in the direction of the moving objects and the fast component back to the midline.

Regarding the proprioceptive system, proprioceptive inputs will aid in static and dynamic postural control primarily through two reflex arcs. The first is the myototic reflex (deep tendon reflex), in which stretch on a muscle causes contraction of the muscle. The myototic reflex serves to maintain stability across a joint. The second proprioceptive reflex arc that aids in posture control is the functional stretch response, which utilizes multiple somatosensory inputs to provide for coordinated limb and trunk movements across joints, for instance to maintain the center of gravity over the support base in an individual who is bumped from behind. This reflex pathway has a higher latency than the myototic reflex, although both are mediated through spinal pathways. Both of these reflex arcs have lower latencies than visual-postural reflexes and vestibular-postural reflexes.

Regarding the vestibular system, the vestibular system consists of two groups of specialized sensory receptors: the semicircular canals and the otolithic organs. The semicircular canals detect angular acceleration of the head. The three semicircular canals consist of a membranous semicircle with a widened area, the ampulla, at one end. The ampulla contains the crista ampullaris: specialized ciliated cells (several small cilia and one large eccentric kinocilium on each cell) jutting into the lumen of the ampulla. The cilia are embedded in a gelatinous structure called the cupula. The membranous semicircular canal contains endolymph (extracellular fluid with a high potassium concentration) that is the same specific gravity as the cupula. When angular acceleration of the head occurs in the plane of the semicircular canal, the endolymph's momentum causes it to stay relatively stationary, displacing the cupula slightly. The cupula then displaces the cilia, causing a decrease in the firing rate of the associated vestibular nerve if the cilia bend away from their kinocilium and an increase in vestibular nerve firing if the cilia bend toward their kinocilium. There are 6 total semicircular canals (three in each inner ear): paired lateral, superior and posterior. The lateral semicircular canals have a plane that is elevated 30 degrees from the coronal. The posterior and superior semicircular canals are in planes that are approximately 90 degrees from each other and both are laterally askew from the sagital plane. The superior (a.k.a. anterior) canal on one side is on the same plane as the posterior canal on the other side, and so detects angular acceleration in the same plane. The ampulla and kinocilia in the *crista ampullaris* of the lateral semicircular canal are arranged in such a way that ampullopetal flow of endolymph causes increased firing of the vestibular nerve and ampullofugal flow decreases the firing of the vestibular nerve. The arrangement is opposite to this in the posterior and superior canal, with ampulopetal flow leading to inhibition of the associated vestibular nerve branch and ampulofugal flow leading to excitation. The end result is the same though: when head is turned towards the side of the semicircular canal (in its plane), that side's vestibular nerve is excited and the opposite paired side's nerve is inhibited. The range of response in excitation of a nerve is greater than the range of response in inhibition. Therefore, both vestibular nerves are generally required to sense acceleration without any detectable deficit.

The otolithic organs consist of a utricle, which is oriented the axial plane, and a saccule, which is oriented in the sagittal plane. These structures contain ciliated cells underneath a gelatinous layer and are bathed in endolymph. They also contain otoconia, which are calcium carbonate crystals of a higher specific gravity than endolymph. The otoconia are displaced in response to changes in head position with relation to the vertical. The otolithic organs also respond to linear acceleration. The ciliated cells can inhibit or excite the vestibular nerve, depending on the direction of their bend in relation to the kinocilium (away=inhibition, towards=excitation).

The vestibular system can affect posture via vestibulospinal pathways. These pathways, in conjunction with visual-postural and proprioceptive-postural pathways, serve to maintain the patient's center of gravity over the base of support. For instance a quick head tilt to the right causes extension of right sided leg extenders to counteract a change in the perceived center of gravity. A perceived forward motion causes a sway forward to maintain the support base. The vestibulo-ocular reflex is a system that maintains the stability of the visual field in response to acceleration of the head in a particular direction. The pathway is from vestibule to vestibular nuclei to the ocular motor nuclei, with modulation from cerebellar centers. The reflex results in movement of the eye so that the fovea can focus the same image during movement of the head. Thus the eye rotates (including tortional rotation) in an exactly opposing fashion to the head. When the eye's rotational limit is exceeded, a saccade brings the eye back to the midline. For example, rotation of the head (nose) to the left would result in excitation of the left branch of the vestibular nerve that innervates the left semicircular canal and in inhibition of the right semicircular canal branch. This combination of excitation and inhibition is passed through the reflex arc and is translated into excitation of the ocular muscles to rotate the eye to the right in an exactly opposing fashion to the head rotation until no longer possible, at which point a saccade brings the eye back to the midline. The process then repeats itself until the angular acceleration ceases.

The vestibular system is a very important system in the conscious sensation of acceleration. Peripheral or central damage to the vestibular system would lead to a severe sense of imbalance until compensation occurs. Also, they would result in measurable alterations of the vestibulo-spinal and vestibulo-ocular reflexes until compensation occurs. Compensation in peripheral vestibular injury is via adjustment of the gain of vestibular reflexes in the cerebellum and modification of signal delivery to supratentorial centers.

There is a growing need, both in the US and worldwide, to improve the health care provided for people who suffer from hearing, balance, and vestibular function disorders. Ninety million Americans go to their health care providers because of vertigo, dizziness or balance problems each year. In the general population, 20% is estimated to be affected by a vestibular disorder with the prevalence increasing with age according to a University of Iowa Health Care study. Hearing and balance problems are the third ranking chronic condition in the older population, yet 75% of those who have a hearing and/or balance disorder are not addressing this issue properly. Dizziness or loss of balance, which the National Institutes of Health estimates will occur in 70% of the nation's population at some time in their lives, is the second most common complaint heard in physicians' offices.

The elderly represent a substantial and growing segment of the population suffering from balance disorders. According to the Department of Otolaryngology at the University of Kansas, approximately 12.5 million Americans over the age of 65 have dizziness or balance problems that significantly interfere with their lives. The increasing elderly population, the rising cost of care, and the need for an expansion of treatment protocols, underscore a growing interest in the vestibular field. More importantly, they are leading to a substantial increase in the need for new technologies and delivery mechanisms that improve vestibular assessment and care.

In the ocular and the vestibular testing field, a wide variety of lighting devices have been developed for providing visual stimuli to the patient for testing. For example Neuro Kinetics, Inc. has provided, since the early 1990's, a laser light device for use with a vestibular testing rotary chair. This laser device was called the Pursuit Tracker™ device. The slow response time of the device (cycle time of about 50 Hz, acceleration of about 1000 degrees/second2 and velocity of about 1200 degrees/second) limited the applications of this device. The prior art device had a position accuracy and repeatability of about 1-2 degrees. Consequently the applications of this device were for testing in which a single visual point or marker was utilized (the single point of the prior Pursuit Tracker™ device could be moved to provide a moving marker to the patient).

There is a need in the industry to provide a compact neuro-otologic testing device producing rapid response or fast cycling (e.g. faster than 75 mille-seconds) shapes and images and in which the motion of the display may be easily matched to the motion of the patient. There is a further need in the industry to develop testing to exploit this technology to provide new tools for neuro-otologic testing and treatment.

Turning to a specific application of the testing platform of the present invention, aircraft pilots, ground vehicle drivers and marine craft skippers all must operate effectively in a physically and visually complex and dynamic environment. Just as critically, the myriad equipment operators, passengers, and support personnel on these different platforms must also be able to perform their function whenever called on. Errors and failures due to motion sickness, whether arising from a natural predisposition or solely from the environment, must be reduced to save lives, equipment and money. Research by the United States Navy has identified that 13.5% of aircrew experienced motion sickness. In a study of Royal Air Force student pilots 15% of the students experienced motion sickness that was severe enough for the flight to be abandoned. The pilot student motion sickness can lead to costly delays in the flying training, and problems associated with student's low self-esteem. For non-pilot aircrew, the probability of becoming motion sick is much higher than for pilots if the motion/visual stimulus is severe enough. Paratroopers experience higher (between 10 to 75%) rate of motion sickness.

While motion sickness in student pilots is not uncommon, it occurs in relatively controlled environments with significant safety systems in place. Once training is completed, the risks of motion sickness can remain a problem. The affected aircrew member can become a liability to the crew and a potential flight safety hazard, depending on the nature and circumstances prevailing at the time. It has been observed that pilots exposed to motion and visual stimuli may eventually become adapted to the stimuli and their motion sickness substantially reduced and at times even disappears. This indicates that treatment and effective screening may be possible.

Three classes of treatments for individuals who suffer from motion sickness exist—behavioral treatments, pharmacological treatment, and desensitization programs.

Behavior Treatments—Biofeedback training, relaxation and psychological counseling can achieve a success rate of up to 40% by reducing the conflict between visual and motion stimuli. For example, motion-affected individuals can view a stable visual reference (such as the horizon), as this will minimize the visual-vestibular conflict. While this is an effective in some cases, it is not generally applicable to military operating environments where constant attention to nearby displays, operation in confined spaces, or operation in the dark may be required.

Pharmacological Treatments—A variety of anti-motion sickness medications have been used to assist pilots in training and other personnel. They are not suited for chronic use, and due to the anti-cholinergic side effect, they are not acceptable for use by solo pilots. They are, however, acceptable for short-term use in student pilots in order to allow them to become adapted to their new three-dimensional operating environment while flying with an instructor. It has been determined that use of medications does not suppress the eventual acquisition of the motion-adapted state, and may actually facilitate adaptation by allowing continued motion exposure and reducing anxiety during the desensitization period.

Desensitization Programs—Many air forces around the world use desensitization programs for the treatment of chronic and intractable motion sickness. Desensitization exploits the fact that repeated exposure to a motion stimulus eventually results in a degree of protective adaptation being conferred on the individual. Desensitization programs generally involve a gradual, incremental exposure on a repetitive basis to a provocative motion stimulus. The motion most often utilized in such programs is the cross-coupled or Coriolis phenomenon. Such a program generally takes a number of weeks to complete, largely determined by how quickly the individual adapts to increasing speeds of rotation. In the Royal Air Force, the ground-based Coriolis stimulation is followed by a flying phase, which consists of a structured program of increasingly provocative and aggressive maneuvering in a jet training aircraft. The success rate of the RAF program is a return to flying of 85%.

The United States military also has a desensitization program, which incorporates the use of biofeedback to enhance the efficacy of the training, with a reported success rate of 79%. The individual who has undergone desensitization must return to the dynamic flight environment as soon after the program is completed for lasting benefit. Any significant delays to the resumption of flying training may lead to loss of the protective adaptation to motion achieved through the desensitization program.

The desensitization approach is the most attractive, since it can be adapted to mimic military requirements, unlike the behavior treatments, and does not have the negative side effects or time restriction of drug treatments. However, objectively measuring subject performance, both prior to and during treatment, is still difficult. Without such a measurement, effectively implementing and evaluating screening and desensitization efforts is impossible.

As early as the 1980s, it has been demonstrated that patients with vestibulotoxicity had difficulty reading standardized acuity charts during active head movements performed at the bedside. There have been some commercial versions of a dynamic visual acuity (DVA) test, all using active patient head movements. These prior DVA tests, as a screening test for vestibular function, have been studied for the aviation community. High frequency voluntary head rotation (i.e. the patient vigorously shakes his head back and forth) was selected as a vestibular stimulus to isolate (VOR) from visual influence. It was determined that DVA tests at frequencies ~2 Hz can be used to evaluate vestibular function. Studies have determined that DVA tests during imposed head motion are a quantitative and clinically feasible measure of oscillopsia reflecting functionally significant abnormalities of the VOR. Further studies have shown that DVA measured during forced head-on-body or whole-body transient motion can correlate closely with VOR performance only if optotypes are presented during directionally and temporally unpredictable, high-acceleration head motion. From these past results, the inventor of the present invention believes that performing DVA testing while the subject is experiencing a simulated operating environment will provide a measure of performance, and performance improvements due to a desensitization program.

It is one object of the present invention to provide an efficient, effective integrated system, consisting of motion simulator and DVA testing subsystems, that may be used for determining the susceptibility of personnel to motion sickness, and also for desensitization treatments. An object of the present invention is that such a platform will provide a screening function that will save time and money by identifying people with severe or intractable problems early. The rehabilitation function of such a platform can safely help the personnel and verify readiness to return to operations. It is a further object of the invention that such a combined system be fully integrated, rugged, portable, easy to use by nonexperts, and fully validated. It should be capable of simulating real operating conditions, including helmets and other gear the personnel will be using.

SUMMARY OF THE INVENTION

The above objects are achieved with a compact neuro-otologic testing device and method of utilizing the same according to the present invention. The device according to the present invention provides an image producing laser with a right hand, servo controlled galvanometric based XY interface. The high quality closed loop servo control system that can drive the target (i.e. the laser image) in excess of 1,000,000 degrees/second$^2$ and at velocities in excess of 12000 degrees/second. The bandwidth of the XY interface is greater than 400 Hz, providing high image reproducibility. The repeatability and position accuracy of the target is +−3 arc-seconds and the field of range of the XY interface are about 60 degrees (i.e. about 60 degrees horizontal and 60 degrees vertical).

The device of the present invention allows a single device to be utilized in a wide variety of tests and for the development of new testing procedures. The device can be easily attached to systems for inputting motion to a patient (as opposed to having the patient induce motion such as by vigorous head shaking). This attachment allows for the image to be moved with the patient, or displayed at a fixed location. The rapid response time allows the device to be utilized for testing in which a visual stimulus is only displayed to the patient for a minimum time. The device can be used to display a shape or symbol that is indicative of the patient's perceived orientation (e.g. ask patient to identify when a rotating line or arrow is horizontal or vertical). The device can be used to implement many existing tests such as smooth pursuit tracking tests.

These and other advantages of the present invention will be clarified in the description of the preferred embodiments taken together with the attached drawings in which like reference numerals represent like elements throughout.

DETAILED DESCRIPTION OF THE PREFERRED EMBODIMENT

Figure 1:
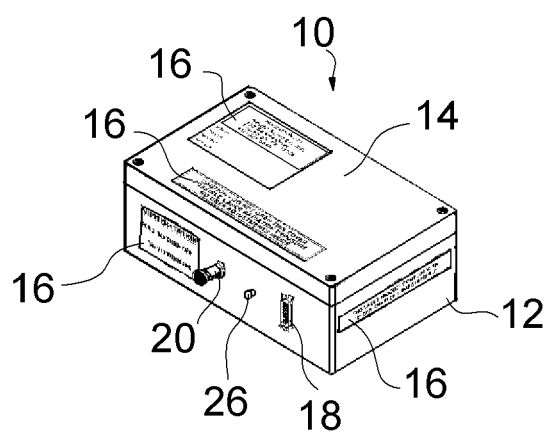
FIG. 1 is a rear perspective view of a compact neuro-otologic, neuro-opthalmologic testing device according to one embodiment of the present invention.
Figure 2:
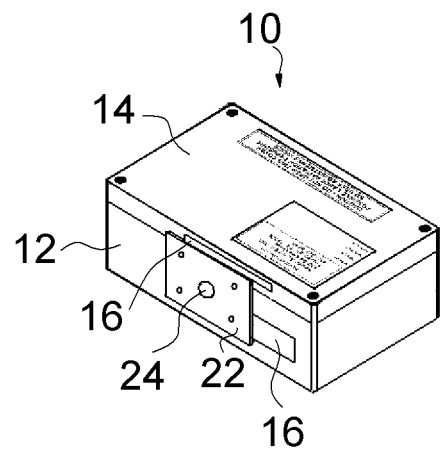
FIG. 2 is a front perspective view of the compact neuro-otologic, neuro-opthalmologic testing device of FIG. 1.
Figure 3:
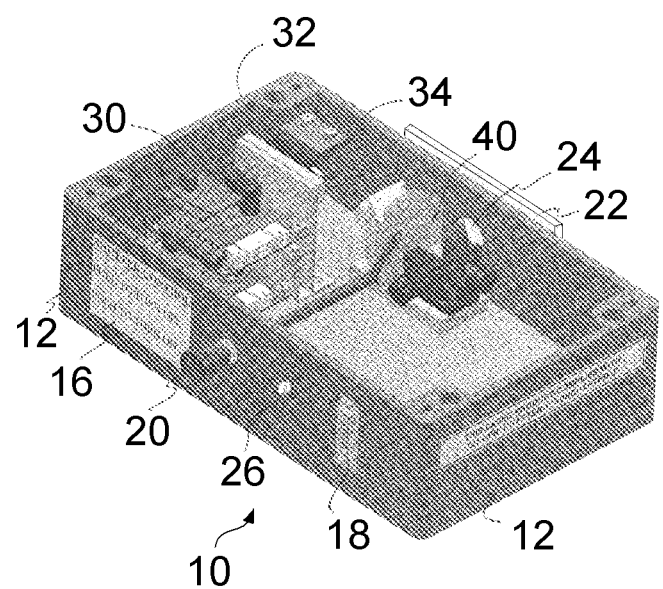
FIG. 3 is a rear perspective view similar to FIG. 1, with a portion of the housing removed, of the compact neuro-otologic, neuro-opthalmologic testing device of FIG. 1.
Figure 4:
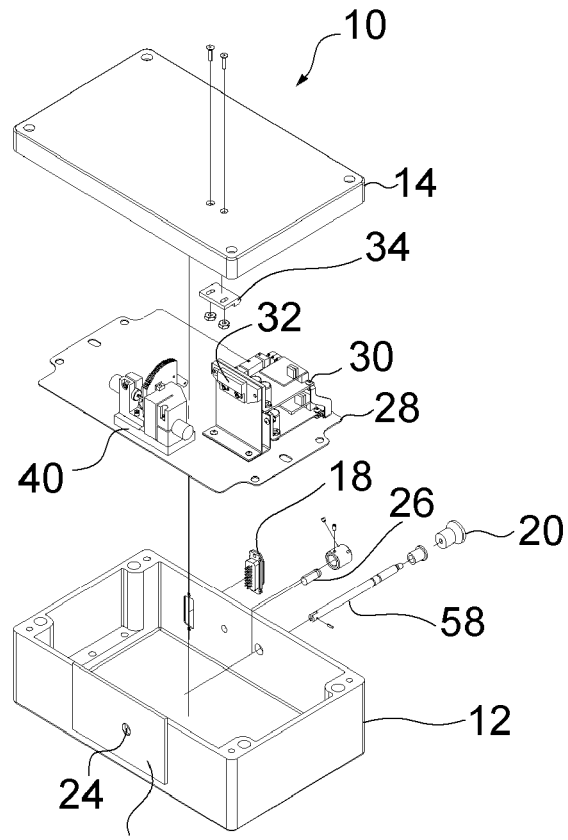
FIG. 4 is an exploded view of the compact neuro-otologic, neuro-opthalmologic testing device of FIG. 1.

As shown in FIGS. 1-6 the compact neuro-otologic, neuro-opthalmologic testing device 10 according to the present invention provides a compact, rapid response laser visual image to the patient for neurological and otological diagnosis and testing. The device 10 is formed in a rectangular housing (having dimensions of or less than about 6"×4"×3") including a base 12 and a lid 14, such as sold by Hoffman Corporation. The housing need not be rectangular and can be any desired shape. The housing could be formed as or in the headrest or armrest of a diagnostic chair, such as a rotary chair sold by Neuro Kinetics, Inc. The compact design of the device 10 allows the device to be easily incorporated into other structures, if desired.

The housing of the device 10 includes appropriate labeling 16 for instructions, warnings, and company branding. The housing may further include a safety mechanism incorporated therein to prevent operation without the lid 12 properly on the base 14. Specifically a proximity switch, such as a magnetic switch, (discussed below in detail) can be positioned on the lid 12 and the base 14 such that the device 10 is switched off unless the Lid 12 is positioned on the base 14. That is the power runs through the proximity switch, which if open, turns off the device 10.

The housing includes an opening for power and communications access as shown by the connector 18 providing a data and power coupling for the device 10. The typical input voltage is 15-28 VDC, with a current of 5 Amps and an input command of +−10 VDC for full X and Y displacement. The housing further includes an opening in base 12 for an external shutter control 20. The base 12 includes an aperture plate 22 having laser opening 24 therein. The aperture plate 22 allows the laser opening 24 to be sized as desired (a larger or smaller or specially shaped opening 24 can be easily provided through the use of a replacement aperture plate 22. The base 12 further includes an opening for an activity or signal light 26 (e.g. a green LED) which provides visual indication that the power to the device 10 is on. Other openings, such as mounting holes or the like, are and can be provided in the housing as needed A subassembly panel 28 is mounted in the base 12 and provides a mounting platform for the components of the device 10. The electrical control components 30 are mounted on the panel 28. The mounting of the electrical components 30 also serves as a convenient location for mounting the base portion 32 of the proximity switch discussed above. A lid portion 34 of the proximity switch is positioned in an aligned location on the lid 12. As shown the electrical control components 30 essentially includes a separate control panel for each of the X and Y positioning motors of the XY interface discussed below. The electrical control components 30 will also provide electrical on/off signals to the laser, which is distinct from the mechanical shut off (i.e. a shutter). The details of the electrical control components 30 will be known to those of ordinary skill in the art need not be described herein in detail. For example, FIG. 7 illustrates an embodiment in which the electrical control components 30 are separated into two metal mounting blocks 38 on the panel 28. The two metal (e.g. aluminum) mounting blocks 38 allow for two separate heat sinks for the components therein, with one grouping of components generally being for the X motor control and the other being for Y motor control (laser control signals will also be with one grouping of control electronic components). Further, as should be apparent from the figures, the device 10 could be constructed with the electrical control components 30 removed from the mechanical sub-assembly 40 (shown in FIGS. 5-6). This possible separation would allow the image producing component to be very minimally sized.

Figure 5:
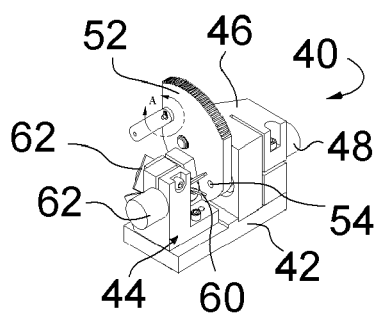
FIG. 5 is a perspective view of the mechanical laser control subassembly for the compact neuro-otologic, neuro-opthalmologic testing device of FIG. 1.
Figure 6:
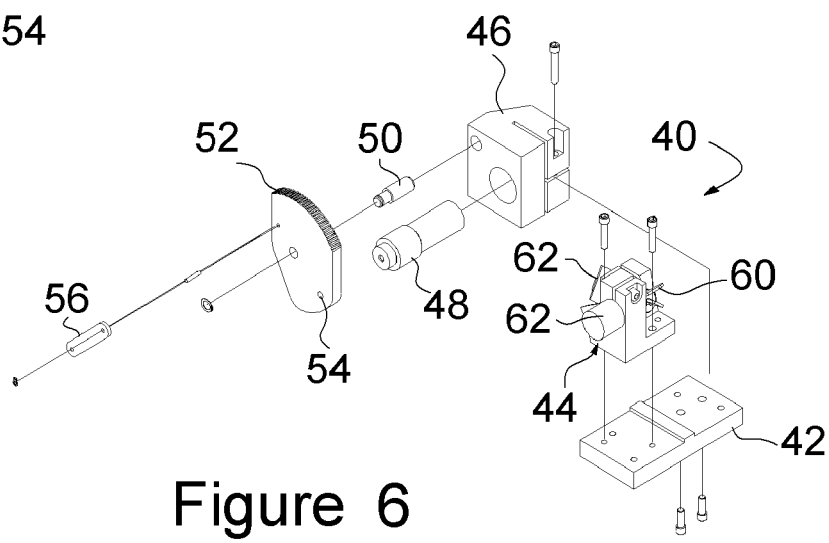
FIG. 6 is an exploded view of the mechanical laser control subassembly of FIG. 5 for the compact neuro-otologic, neuro-opthalmologic testing device of FIG. 1.
Figure 7:
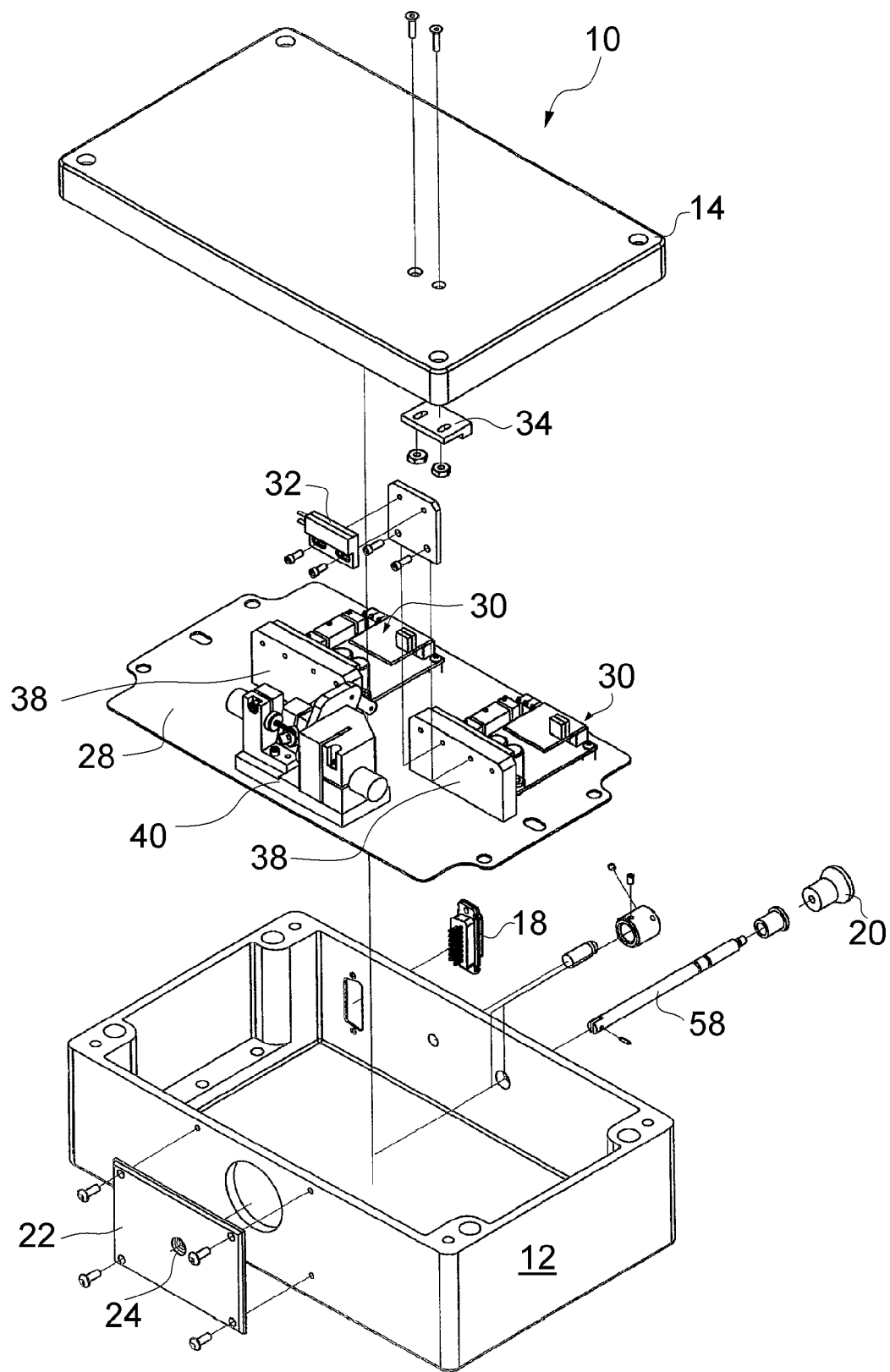
FIG. 7 is an exploded view, similar to FIG. 4, of a modified neuro-otologic, neuro-opthalmologic testing device according to the present invention.

The mechanical subassembly 40 is shown in detail in FIGS. 5-6 and includes a mounting block 42 with an XY interface 44 on one side of the block 42 and a laser holder 46 n the other. The laser holder 46 mounts a laser 48 therein and provides a pivot mount 50 for a mechanical dial shutter 52. The laser 48 is a low power (less than 1 mW), surge protected, static protected, reverse polarity protected, solid state laser sold by Diode Laser Concepts, but can be any number of acceptable laser optical devices acceptable for generating a viewable image. The image is a bright red 3 mm diameter circle. The laser 48 provides a compact, lightweight light source with durable, long, reliable emitting life, low power consumption and minimal heat generation. The laser 48 provides for maintenance of image size and quality on any smooth imaging surface (e.g. screen or wall) up to 100 feet from the aperture 24.

The shutter 52 includes a opening 54 which is aligned with the laser 48 when the shutter 52 is in the open position. A linkage arm 56 attaches the shutter 52 to an actuation rod 58 extending through the opening in the base 12 to the control knob 20. Axial movement of the rod 58 by the operator will pivot the shutter 52 between open and closed positions. The rod 58 is axially pushed forward to align the opening 54 with the laser 48 and pulled back to pivot the shutter 52 to a position blocking the laser 48 (i.e. where the opening 54 is not aligned with the laser 48). Stops, not shown, can be provided on the laser holder 46 or the mounting block 42 to limit the pivoting motion of the shutter 52.

The XY interface 44 is a right hand, servo controlled galvanometric based XY interface as shown and is available from Cambridge Technologies. The XY interface 44 has a pair of associated pivoting mirrors 60 which are aligned to receive the light from the laser 48 (when the shutter 52 is in the open position and the laser 48 is on) and project it through the opening 24. Each mirror 60 may be effectively formed as high performance dielectric coded, fused silica mirrors which essential eliminate visual image distortion in the reflected image. The angular position of each mirror 60 is precisely controlled by a motor 62. Essentially, one of the mirrors 60 will control the position of the light exiting the aperture 24 in a first direction (an X-axis) and the second mirror 62 will control the position of the light exiting the aperture 24 in a second direction (a Y-axis) orthogonal to the first direction. The XY interface, together with the electronic control components 30 form a high quality closed loop servo control system that can drive the target (i.e. the laser image) in excess of 1,000,000 degrees/second 2 and at velocities in excess of 12000 degrees/second. The bandwidth of the XY interface is greater than 400 hz, providing high image reproducibility. The repeatability and position accuracy of the target is +−3 arc-seconds and the field of range of the XY interface are about 60 degrees (i.e. about 60 degrees horizontal and 60 degrees vertical).

The XY interface 44 allows a shape or an image to be presented to the patient as opposed to a single point of light. The image can be a single line, an arrow, a cross hair pattern, a C or E pattern, which are some of the common images used for otological or neurological testing. A more complex pattern is, of course, possible with the specific pattern being designed for the specific testing desired. Further these images can be rotated or orientated in any fashion which can also play an important role in the testing as discussed below. For example the test may simply ask the patient which way the opening of a letter is facing (up, down, left or right), or a patient may be asked to pivot a line until it is horizontal or vertically aligned. The ability to produce an image is provided by the closed loop servo control system that can drive accelerations in excess of 1,000,000 degree/second2 and velocities in excess of 12000 degrees/second. Further the entire image can be cycled in less than 75 mili-seconds. The device 10 provides a single apparatus for calibration, smooth pursuit tracking and saccadic motion.

The uses of the device 10 may best be explored with a representative example of applications thereof. Dynamic Visual Acuity (DVA) refers to an observer's ability to resolve a critical detail in a visual target under conditions of relative motion between an observer and a target. Dynamic Visual Acuity test assesses impairments in a patient ability to perceive objects accurately while is head is actively moving. In individuals with Vestibular Ocular Reflex (VOR) problems (as noted above, this is the reflex that allows us to keep the image we are looking at on the retina during head movement so that the image will be sharp and clear) dynamic visual acuity degrade during test movement. It was established than DVA test can be indicate patients with underlying VOR pathology.

The vestibular-ocular reflex stabilizes vision by eliciting compensatory eye movements in the opposite direction of head movements. This reflex is especially important during rapid head motions (>1.2 Hz) that visual following mechanisms alone cannot adequately compensate for. However, with most motion environments, such as riding in cars and planes, the VOR must be suppressed to fixate on scenes that are moving with the head, such as reading a book or looking at cockpit instrumentation. Motion sickness in this case can often result from visual-vestibular conflict over competing reflexes. Research made by National Highway Traffic Safety Administration (US Department of Transportation) demonstrates than drivers with crashes shows significantly lower DVA performance compare with control group.

Figure 8:
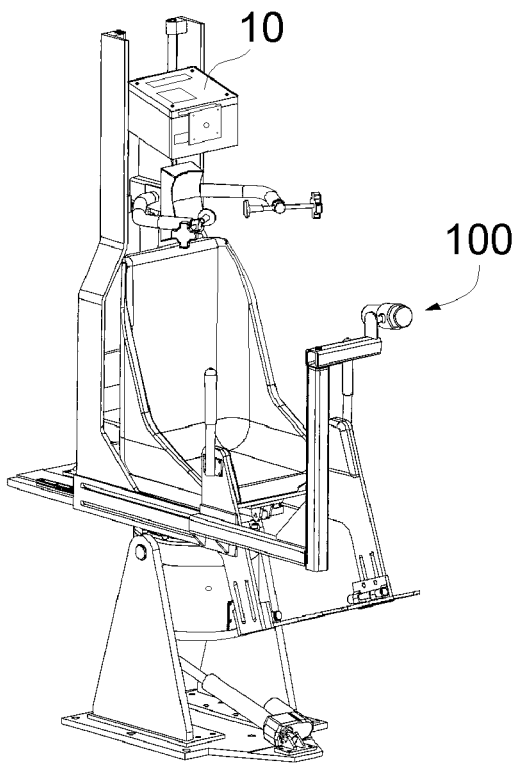
FIG. 8 is a schematic view of the compact neuro-otologic, neuro-opthalmologic testing device of FIG. 1 combined with a rotary chair providing a dynamic visual acuity testing and desensitization platform.
Figure 9:
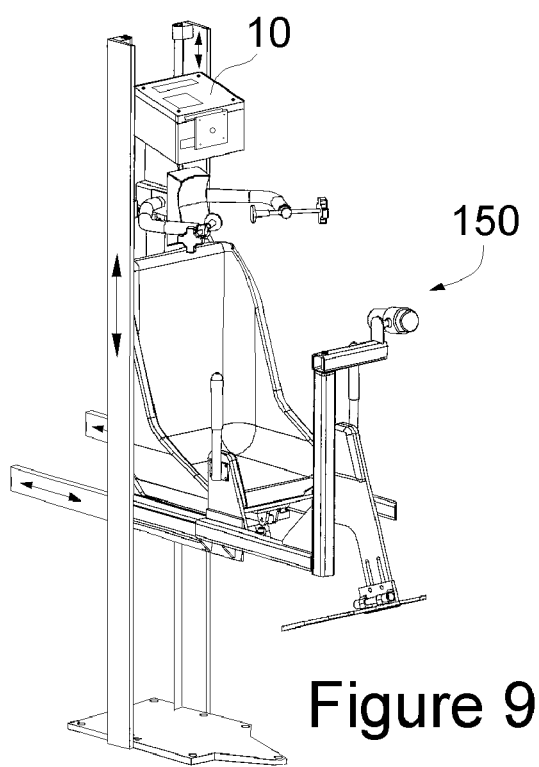
FIG. 9 is a schematic view of the compact neuro-otologic, neuro-opthalmologic testing device of FIG. 1 combined with a linear moving chair providing a dynamic visual acuity testing and desensitization platform.

The use of the device 10 in a DVA test may allow a direct measure of visual acuity without the burden of recording eye movements, although the present invention does not prohibit or inhibit the recording of eye movement. The device 10 would be mounted on a device imparting motion to the patient (e.g. a rotary chair 100 as shown in FIG. 8). Visual acuity measures are common in society, routinely occurring during health checkups and driving examinations. More importantly, visual acuity will provide a functional measure that can be used assess how decrements in visual or vestibular reflexes influence a patient's ability to perform daily activities. A unique feature of the DVA test with the device 10 is that the motion stimulus (e.g. through a chair or other motion imparting device) should be passively driven as opposed to active by the patient (e.g. shaking his head). This has several advantages over the current testing technology. First, both the motion stimuli and visual stimuli can be computerized and therefore not dependent on a patient's ability to perform difficult head movements. More importantly, the visual stimuli can be presented at any specified time through the device 10 relative to the motion (as opposed to the current technology that restricts the visual stimulus to be presented only when the patient is facing the display). This allows us to present visual optotypes, or laser generated images, (e.g. characters) that move with the head, thus allowing a functional assessment of VOR suppression. This Dynamic Visual-Vestibular Acuity Test will present visual optotypes that are either projected to the same location on the wall (normal VOR test) or moving with the subject (VOR suppression). The motion stimuli will consist of small oscillations (<30 deg from center) over a frequency range of 0.1 to 2.0 Hz. This test can either be incorporated as upgrades into existing rotary chairs 100, such as sold by Neuro Kinetics Inc., or as part of a new system that will provide small vertical and/or linear displacements similar to what might be encountered in automobile or aviation motion environments such as shown in FIG. 9. FIG. 9 illustrates a system 150 with a device 10 including a patient chair that can rapidly move along vertical and/or horizontal tracks, as desired. In addition to providing a new functional assessment tool, the device 10 can be utilized for motion sickness desensitization.

Figure 10:
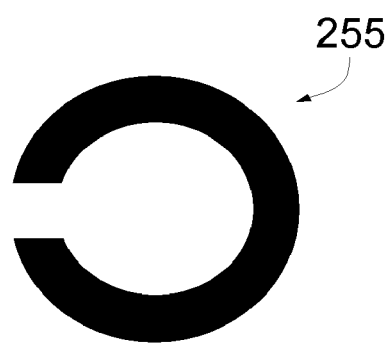
FIG. 10 is a schematic view a representative of an ototype that can be used in a dynamic visual acuity testing and desensitization platform according to the present invention.

A more detailed review of the application of the device 10 on an existing rotary chair 100 may be helpful for clarification. In such an arrangement the operator can begin with a static visual acuity test with the system defaulting to logMAR 0 (equivalent to Snellen 20/20). Each optotype size will be presented up to 5 times. An example of an optotype 200 is shown in FIG. 10, and it will be understood that the gap in the optotype 255 can be in any of 4 or 8 (or any predefined number) that the user must identify. The subject response will be forced choice (entered by operator). If incorrect 3 of 5 times, then the optotype will increase size by one level. If correct 3 of 5 times, then the optotype will decrease size by one level. This will continue until determining the minimal logMAR size that the subject responds correctly 3 of 5 times.

A DVVAT protocol would follow the static test with the DVVAT protocol sequence similar to static visual acuity above, except with varying chair and visual motion. During chair oscillation, the presented letters will be either fixed relative to the surround (at same mid-point location), or fixed relative to the head (i.e., moving with the chair). The four motion stimuli conditions are: (1) chair oscillating in darkness, (2) chair oscillating with static visual background, (3) chair and visual surround oscillating together, or (4) chair stationary and visual surround oscillating. One objective is to compare acuity when the letters are fixed relative to the surround (assessing normal visual-vestibular reflex function) or fixed relative to the head (assessing the suppression of visual-vestibular reflexes). Another objective is to obtain separate measures during motion to the right or left so that asymmetries for unilateral vestibular patients may be obtained. Presenting the targets at different points in the rotation cycle (phased in 45 deg increments) and different reference points (head versus surround) will minimize predictive strategies.

The default frequency for the chair and visual surround motion will be 0.3 Hz with 40-deg/sec-peak velocity (±21 deg displacements).

Visual desensitization training with the device 10 may consist of 60 sec exposures to an optokinetic stimulus (OKS) of 30 deg/sec in one direction, followed by 60 sec at rest, and then 60 sec exposure in the opposite direction. This will be repeated until the onset of visual vertigo and/or slight motion sickness symptoms. During each 60 sec period, 5 optotypes will be presented at 10, 20, 30, 40, and 50 sec. No response within the 10 sec answer period will automatically be scored as incorrect. The acuity level will be preset by the operator initially at +0.2 logMAR steps above static visual acuity. Acuity will be tracked separately for three OKS conditions: leftward OKS, rightward OKS and static OKS. If incorrect 3 of 5 times, then the optotype will increase size by one level the next time that OKS condition occurs. If correct 3 of 5 times, then the optotype will decrease size by one level the next time that OKS condition occurs. Note that the optotype size will vary from one trial to the next, either increasing or decreasing in size depending on performance.

The uses of the device 10 can be used in numerous existing tests, and the unique abilities of the device 10 allow for the technician to develop future tests. A further listing of the known tests that can be easily conducted with the device 10 of the present invention is a Calibration test, a Spontaneous Nystagmous test, a Smooth Pursuit Horizontal Sinusoid test, a Smooth Pursuit Vertical Sinusoid test, a Smooth Pursuit Horizontal Trapezoidal test, a Smooth Pursuit Horizontal Trapezoidal test, a Horizontal Gaze test, a Vertical Gaze test, a Horizontal and/or Vertical Saccade test, a Visual Suppression test, a Visual Enhancement test (requires a rotary chair), a Subjective Visual Horizontal, and a Subjective Visual Vertical test. The specific tests and needed visual images necessary to be displayed to the patient (and under what conditions) will be know to those of ordinary skill in the art. A key feature of the present invention is that a single compact device 10 can provide all of these tests in a single unit.

It will be apparent to those of ordinary skill in the art that various modifications may be made to the present invention without departing from the spirit and scope thereof. For example, the present invention contemplates using the device 10 to project a preformed image for the patient (as opposed to rapidly forming the visual image). The use of a laser to project a holographic image from a slide has been proposed. One modification of the device 10 is to use such slide in front of the laser 48 to project desired holographic images. In implementation of this concept the laser holder 46 would include a slot for receiving the slide to be projected (or one of a series of slides such as in a rotating carousel slide holder). In this manner the laser would be used to project a desired image from the slide (as opposed to the formation of the image described above).

What is claimed is:

1. A Dynamic Visual Vestibular Acuity Testing protocol of for testing an observer's ability to resolve a critical detail in a visual target under conditions of relative movement, said protocol comprising the steps of providing passive oscillation movement to the patient during testing through a movement mechanism; and displaying a laser based visual optotype images in the form of a non-circular optotype as a visual target to the patient during testing from a testing device including a housing having a laser opening therein and mounted on the mechanism for providing passive movement to the patient, an image producing laser mounted within the housing adapted to project through the laser opening to form the visual target image for testing the observer's ability to resolve a critical detail in the visual target under conditions of relative movement, wherein the laser forming the image is controlled by a galvanometric based XY interface having a closed loop servo control system that can drive the image in excess of 1,000,000 degrees/second$^2$ and at velocities in excess of 12000 degrees/second.

2. A Dynamic Visual Vestibular Acuity Testing protocol of for testing an observer's ability to resolve a critical detail in a visual target under conditions of relative movement, said protocol comprising the steps of providing passive oscillation movement to the patient during testing through a movement mechanism; and displaying a laser based visual optotype images in the form of a non-circular optotype as a visual target to the patient during testing from a testing device including a housing having a laser opening therein and mounted on the mechanism for providing passive movement to the patient, an image producing laser mounted within the housing adapted to project through the laser opening to form the visual target image for testing the observer's ability to resolve a critical detail in the visual target under conditions of relative movement, wherein the laser forming the image is controlled by an XY interface that can drive the image in excess of 1,000,000 degrees/second$^2$ and at velocities in excess of 12000 degrees/second, and wherein each optotype image can be displayed in at least two visually distinct orientations.

* * * * *